Figure 1:
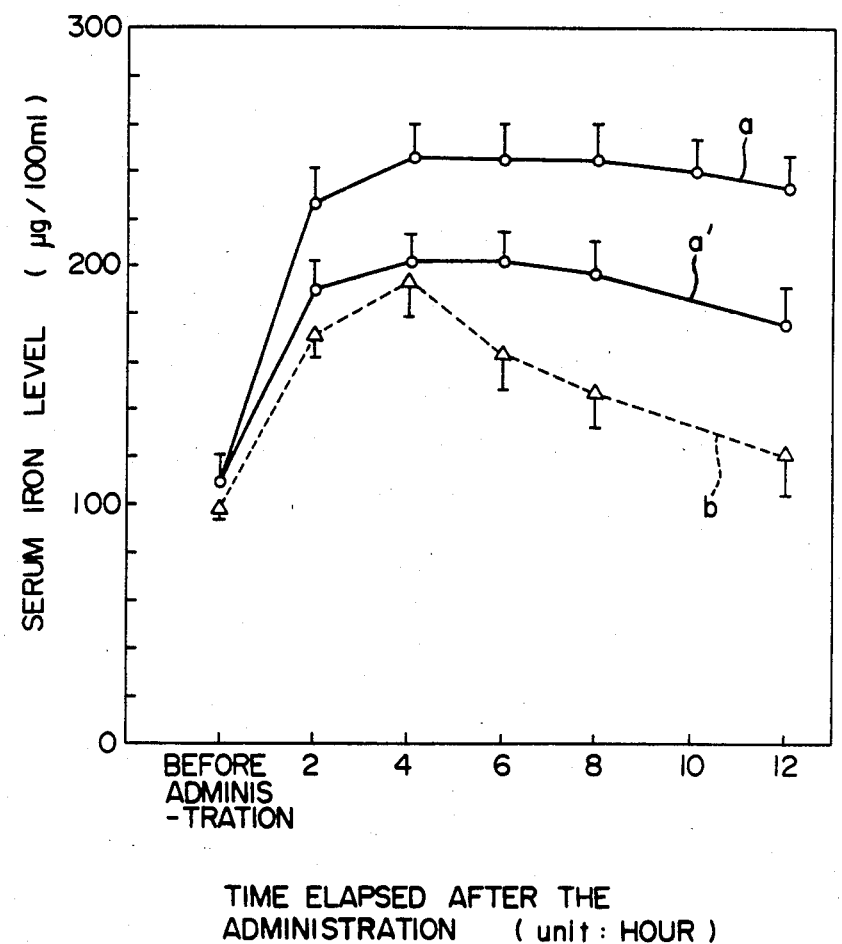

United States Patent [19]

Miyata et al.

[11] Patent Number: 4,629,626

[45] Date of Patent: * Dec. 16, 1986

[54] HYDROTHERMALLY TREATED PRODUCT OF COMPOUND HAVING HYDROTALCITE-LIKE CRYSTAL STRUCTURE COMPOSITION THEREOF, AND USE THEREOF

[75] Inventors: Shigeo Miyata; Hitoshi Anabuki, both of Takamatsu, Japan

[73] Assignee: Kyowa Chemical Industry Co., Ltd., Tokyo, Japan

[*] Notice: The portion of the term of this patent subsequent to Nov. 15, 2000 has been disclaimed.

[21] Appl. No.: 625,244

[22] Filed: Jun. 27, 1984

[30] Foreign Application Priority Data

Jun. 27, 1983 [JP] Japan .................................. 58-114364

[51] Int. Cl.$^4$ ..................... A61K 31/26; A61K 31/295
[52] U.S. Cl. ................... 424/147; 423/419 P; 423/554; 423/594; 514/502; 556/27
[58] Field of Search ........................ 424/147; 514/502; 260/439 R, 448 B, 429 J; 423/419 P, 554, 594

[56] References Cited

U.S. PATENT DOCUMENTS

| | | | |
|---|---|---|---|
| 3,650,704 | 3/1972 | Kumura et al. | 424/154 |
| 3,829,561 | 8/1974 | Heinrich | 424/147 |
| 4,415,555 | 11/1983 | Anabuki et al. | 424/147 |

*Primary Examiner*—Frederick E. Waddell
*Attorney, Agent, or Firm*—Sherman and Shalloway

[57] ABSTRACT

A hydrothermally treated product useful for treating an iron deficiency of a compound having a hydrotalcite-like crystal structure and represented by the following formula (I)

$$(Fe^{2+},Mg^{2+})_x(Al^{3+},Fe^{3+})_2(OH)_{2x+6-n\cdot z}(A^{n-})_z\cdot mH_2O \qquad (I)$$

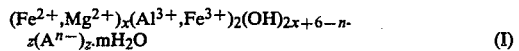

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, z is a number represented by $0 < z < 3$, and m is a number represented by $0 \leq m < 20$, the product being formed by the thermal treatment of the compound of formula (I) at a temperature of about 100° C. to about 200° C. in an aqueous medium.

12 Claims, 1 Drawing Figure

HYDROTHERMALLY TREATED PRODUCT OF COMPOUND HAVING HYDROTALCITE-LIKE CRYSTAL STRUCTURE COMPOSITION THEREOF, AND USE THEREOF

This invention relates to a novel product derived from a known compound having a hydrotalcite-like crystal structure which is useful for treating an iron deficiency syndrome, a composition comprising the novel product, and a method of using the novel product. In particular, the novel products are useful for treating an iron deficiency syndrome, and exhibit excellent activity in the prevention and therapy of various diseases associated with ion deficiency, such as iron deficiency anemia and hypoferremia, with a long-lasting efficacy and markedly reduced side-effects. Furthermore, they have better oxidation resistance (stability) to conventional products and comparable activity to the conventional products. This invention also relates to a composition for increasing at least one of hemoglobin and the serum iron level comprising the novel product, a method for increasing at least one of hemoglobin and the serum iron level, and also to a process for producing the novel product.

More specifically, this invention relates to a hydrothermally treated product of a compound having a hydrotalcite-like crystal structure and represented by the following formula (I)

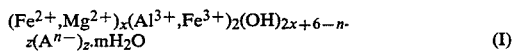
$$(Fe^{2+},Mg^{2+})_x(Al^{3+},Fe^{3+})_2(OH)_{2x+6-n-z}(A^{n-})_z \cdot mH_2O \quad (I)$$

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, z is a number represented by $0 < z < 3$, and m is a number represented by $0 \leq m < 20$, the product being formed by the hydrothermal treatment of the compound of formula (I) at a temperature of about 100° C. to about 200° C. in an aqueous medium.

This invention also relates to a composition for increasing at least one of hemoglobin and the serum iron level, said composition being composed of (1) an amount, effective for increasing at least one of hemoglobin and the serum iron level, of the aforesaid hydrothermally treated product, and (2) a pharmaceutically acceptable diluent or carrier.

This invention also relates to a method for increasing at least one of hemoglobin and the serum iron level, which comprises orally administering an amount, effective for increasing at least one of hemoglobin and the serum iron level, of the aforesaid hydrothermally treated product. The method is useful for preventing and/or treating anemic symptoms particularly iron deficiency syndromes.

This invention also relates to a process for producing the hydrothermally treated product, as will be described hereinbelow.

It is known that the deficiency of iron, an essential ingredient for hemoglobin synthesis in vivo, inhibits the formation of hemoglobin, and causes various anemic symptoms such as general malaise, headache, dizziness, sounding in the ears, pain at the glossal mucous membrane, reduced appetite, epigastralgia, etc. The causes of such iron deficiency include, for example, the lack of iron up-take from foods, the insufficiency of iron absorption due to abnormality or reduction of the function of the stomach and small intestine, the increased demand for iron in vivo during the rapidly growing stage of infants or during pregnancy, and the unusually increased excretion of iron during menstruation or due to bleeding by peptic ulcer or other lesions. It is difficult to make up for such iron deficiency by foods alone because the ratio of iron absorbed by eating is very low and the amount of foods that can be taken is naturally limited. It is the general practice therefore to supply iron by orally or parenterally administering various iron-containing compounds as treating agents for the prevention and therapy of an iron deficiency syndrome.

Various inorganic and organic iron-containing compounds have been used heretofore as treating agents for iron deficiency, but none of them have proved to meet the three important requirements of such treating agents, i.e. high absorption in vivo, long-lasting efficacy, and reduced side-effects.

Iron taken into the body is absorbed in the form of a ferrous ion (divalent) from the duodenum [see, for example, Nakao et al., "Shin Naikagaku Taikei" (Outline of New Internal Medicine), Diseases of Blood and Blood-Forming Organ 1, page 185, published by Nakayama Shoten, Japan], and therefore, such iron-containing compounds are desirably used in the form of an inorganic divalent iron salt such as ferrous sulfate or reduced iron (FeO). These inorganic iron salts, however, have the defect of stimulating the mucous membrane of the stomach and being likely to cause a serious gastric trouble. Since it is common that continued aministration over several months is required for the treatment of iron deficiency, the aforesaid defect sets a marked restriction on the use of inorganic ferrous salts as treating agents for iron deficiency.

In order to eliminate this defect of inorganic ferrous salts for the treatment of iron deficiency, there have been used various organic acid salts of iron which do not permit dissociation of iron in an amount large enough to cause troubles to the mucous membrane of the stomach, and can be ionized in the duodenum which is the site of iron absorption. Examples of such organic acid salts of iron are iron fumarate, iron succinate and iron gluconate. Although these organic acid salts of iron have the advantage of obviating gastric troubles to some extent, they suffer the new defect that the amount of iron absorbed and utilized decreases. This defect makes it necessary to administer these compounds in large amounts. In addition, since the ratio of iron to be absorbed generally decreases with increasing amount of iron administered at a time, the aforesaid need for administration of large amounts makes it difficult to essentially avoid the gastric troubles.

We undertook extensive investigations in order to provide an iron deficiency treating agent of a new type which is free from the defects of the conventional agents for treating iron deficiency.

We consequently found that compounds which overlap the compounds of formula (I) used for the production of the hydrothermally treated product of this invention overcome the aforesaid defects of the conventional agents; exhibit excellent activity in the prevention and treatment of various iron deficiency syndromes such as iron deficiency anemia with a long-lasting efficacy and reduced side-effects; and that these compounds are extremely low in toxicity. Based on this discovery, we filed a patent application covering these compounds as an agent for treating iron deficiency conditions (see Japanese Laid-Open Patent Publication No. 156419/1982 corresponding to U.S. Pat. No. 4,415,555 and European Laid-Open Patent Publication No. 61175A).

The above-cited patent document states that the agent for treating iron deficiency conditions which has a hydrotalcite-like crystal structure is preferably stored in a non-oxidizing atmosphere or in a reducing atmosphere such as hydrogen. Subsequent investigations of the present inventors showed that the above-proposed agent for treating iron deficiency is still desired to be improved in stability. The investigations of the present inventors showed that when the compound of formula (I) described in the prior patent is placed in an oxidizing atmosphere such as air, $Fe^{2+}$ in the compound is oxidized to $Fe^{3+}$, and consequently, the absorption of the compound from the duodenum becomes difficult. To avoid this technical problem, the product dried in a non-oxidizing atmosphere should be immediately stored in a non-oxidizing or reducing atmosphere. Accordingly, improvement was still desired in regard to handling and storage.

The present inventors continued their investigations in order to overcome the aforesaid technical problem of their prior technique. These investigations have led to the discovery that a product obtained by hydrothermally treating a compound of formula (I) having a hydrotalcite-like crystal structure at a temperature of about 100° C. to about 200° C. in an aqueous medium shows markedly improved stability over the untreated compound of formula (I) previously proposed by the present inventors, and retains excellent activity, long-lasting efficacy and reduced side-effects comparable to those of the previously proposed agent.

The present inventors presume that the hydrothermal treatment at about 100° to about 200° C. in the aqueous medium brings about a greater growth of the crystals of the compound of formula (I), a reduction in its surface area and a reduction in lattice defects. It has been found in accordance with this invention that there can be provided an agent for treating iron deficiency conditions which has markedly improved oxidation resistance (stability), is free from the aforesaid handling and storing restrictions of the non-hydrothermally treated compound previously proposed by the present inventors, and has excellent activity in the treatment of iron deficiency conditions which is comparable to that of the previously proposed agent.

It is an object of this invention therefore to provide a novel product derived from a known compound having a hydrotalcite-like crystal structure and represented by formula (I), which is useful for treating an iron deficiency syndrome.

Another object of this invention is to provide a process for preparing the novel product, a composition containing the novel product, and a method of using the novel product.

The above and other objects and advantages of this invention will become more apparent from the following description.

According to this invention, there is provided a hydrothermally treated product of a compound having a hydrotalcite-like crystal structure and represented by the following formula (I)

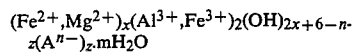
(I)

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, preferably z is a number represented by $0 < z < 3$ preferably and m is a number represented by $0 \leq m < 20$, the product being formed by the thermal treatment of the compound of formula (I) at a temperature of about 100° C. to 200° C. in an aqueous medium.

Examples of preferred anions $A^{n-}$ include $CO_3^{2-}$, $SO_4^{2-}$, $OH^{1-}$, a tartrate anion $[(CHOHCOO)_2^{2-}]$, a gluconate anion $[(CHOH)_4CH_2OHCOO^{1-}]$, a fumarate anion $[C_2H_2(COO)_2^{2-}]$, a succinate anion $[(CH_2COO)_2^{2-}]$, a glucuronate anion $(C_5H_9O_5\text{-}COO^{1-})$, a glycine anion $(CH_2NH_2COO^{1-})$, and a lactate anion $(CH_3CHOHCOO^{1-})$.

Among the compounds expressed by formula (I), those of the following formula (1)' are preferred.

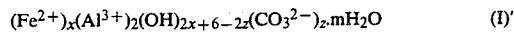
(I)'

In formula (I)', x, z and m are as defined above, and it is especially preferred that x be a number represented by $2.5 \leq x < 8$, especially $3 \leq x \leq 6$, z be a number represented by $1 \leq z \leq 2$, and m be a number represented by $0 \leq m < 20$.

The hydrothermally treated product derived from the compound of formula (I) also has a crystal structure similar to that of hydrotalcite, and the crystal surface is strongly charged positively. The hydrotalcite-like crystal structure, as referred to in this invention, means that the compound of formula (I) or the hydrothermal-treated product thereof shows a diffraction pattern in powder X-ray diffraction (JCPDS No. 14-191) which is substantially identical with, or very similar to, the diffraction pattern of hydrotalcite $[Mg_6Al_2(OH)_{16}CO_3.4H_2O]$. It is observed, that when the anion $A^{n-}$ in the compound of formula (1) or the hydrothermal-treated product thereof is other than $CO_3^{2-}$, its lattice constant $C_o$ shifts depending upon the size (ion radius) of the anion, and that the lattice constant $a_o$ decreases in inverse proportion to the content of Al in response to variations in the mole ratio of Fe:Al. The differences are slight, however.

The hydrothermally treated product of this invention can be produced, for example, by hydrothermally treating the compound having a hydrotalcite-like crystal structure (which can be obtained by the same process as disclosed in the above-cited Japanese Laid-Open Patent Publication No. 156419/1982 (corresponding to U.S. Pat. No. 4,415,555 and European Laid-Open Patent Publication No. 61175A) at a temperature of about 100° C. to about 200° C. in an aqueous medium.

Thus, according to this invention, there is provided a process for producing a hydrothermally treated product useful for the treatment of an iron deficiency syndrome, which comprises (1) reacting (a) an aqueous solution of a water-soluble divalent iron salt or an aqueous solution of a water-soluble divalent iron salt and a water-soluble magnesium compound with (b) an aqueous solution of a water-soluble aluminum compound or an aqueous solution of a water-soluble aluminum compound and a water-soluble trivalent iron salt (c) in the presence of an alkali at a pH of, for example, at least about 6, preferably about 8 to about 12, in the presence or absence of a compound capable of forming an anion $A^{n-}$ having a valence of n, preferably in a non-oxidizing atmosphere, to form a compound having a hydrotalcite-like crystal structure and represented by the following formula (I)

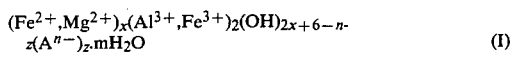

$$(Fe^{2+}, Mg^{2+})_x (Al^{3+}, Fe^{3+})_2 (OH)_{2x+6-n \cdot z} (A^{n-})_z \cdot mH_2O \quad (I)$$

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, z is a number represented by $0 < z < 3$, and m is a number represented by $0 \leq m < 20$, and (2) hydrothermally treating the resulting compound of formula (I) at a temperature of about 100° C. to about 200° C. in an aqueous medium.

Since divalent iron is susceptible to oxidation to trivalent iron even in the presence of a relatively small amount of oxygen, it is preferred to remove dissolved oxygen from the starting aqueous solution as much as possible by known techniques, for example by blowing nitrogen gas or other non-oxidizing inert gases into the solution, before the reaction is carried out.

The reaction of forming the compound of formula (I) is preferably carried out in a non-oxidizing atmosphere, for example in an atmosphere of nitrogen gas or an inert gas containing substantially no oxygen.

The reaction of forming the compound of formula (I) may be carried out, for example, at room temperature to a temperature of about 80° C. The reaction time can be varied properly, and may, for example, be about 20 to about 60 minutes. After the reaction, the reaction mixture is contacted and washed with water, alcohol, etc. preferably under conditions not causing contact with oxygen, or when the compounds (a) and (b) do not contain anion $A^{n-}$, the reaction mixture is contacted with an aqueous solution containing the desired $A^{n-}$ preferably under conditions not causing contact with oxygen. As required, the product is dehydrated, washed with water, etc. and can be dried as required in a nonoxidizing atmosphere or in an atmosphere of nitrogen gas or another inert gas containing substantially no oxygen.

Examples of the water-soluble divalent iron salt used in the above reaction include ferrous sulfate, ferrous chloride, ferrous nitrate, ferrous ammonium sulfate, ferrous lactate, ferrous fumarate and ferrous oxalate.

Examples of the water-soluble magnesium salts include magnesium chloride, magnesium nitrate, magnesium sulfate, magnesium bromide, magnesium acetate, magnesium citrate, magnesium fluoride, magnesium lactate, and magnesium oxalate.

Examples of the water-soluble aluminum compound include aluminum chloride, aluminum nitrate, aluminum bromide, aluminum fluoride, aluminum sulfate, aluminum ammonium sulfate, aluminum potassium sulfate, aluminum isopropoxide, aluminum sodium sulfate, sodium aluminate, potassium aluminate and aluminum acetate.

Examples of the water-soluble trivalent iron salt, include ferric chloride, ferric citrate, ferric sulfate, ferric nitrate, ferric ammonium oxalate and ferric ammonium sulfate.

In performing the above reaction, it is preferred to dissolve the above-exemplified water-soluble salts or compounds in water, for example distilled water from which dissolved oxygen has been removed by blowing a non-oxidizing inert gas such as nitrogen gas, to prepare the starting aqueous solutions (a) and (b). To react the aqueous solutions (a) and (b) in the presence of an alkali, the alkali may be added after the two aqueous solutions have been mixed. Alternatively, the alkali may be added to one or both of these aqueous solutions before they are mixed. The alkali used may of such a type and amount as can maintain the pH of the reaction system at at least about 6, preferably at least about 8, for example at about 8 to about 12. Examples of such alkalies are sodium hydroxide, potassium hydroxide, ammonia gas, sodium carbonate, potassium carbonate and calcium hydroxide. Preferably, the reaction is carried out with sufficient stirring.

Where the aqueous solutions (a) and (b) used in the aforesaid reaction do not contain the desired anion $A^{n-}$, for example a lactate anion, a fumarate anion, a glycine anion or a gluconate anion, the reaction product after the reaction may be contacted with an aqueous solution containing the anion $A^{n-}$, for example an aqueous solution of an alkali metal salt of the anion to perform ion-exchanging reaction and thereby to convert it to a compound containing the desired $A^{n-}$. Or by adding the anion $A^{n-}$ or a compound capable of forming the anion under alkaline conditions to the starting solutions (a) and/or (b) or to the reaction system and then reacting the solutions (a) and (b), a compound of formula (1) containing the desired anion $A^{n-}$ may be formed. The aforesaid anion exchange reaction can be carried out by mixing the reaction product with an aqueous solution of an alkali metal salt of the anion; or by filling the reaction product in a column and passing the aqueous alkali metal solution through the column.

If the pH of the reaction system is lower than about 6, the amount of divalent iron reacted abruptly decreases. If, on the other hand, the pH of the reaction system is higher than about 13, aluminum does not easily participate in the reaction. For this reason, the suitable pH of the reaction system is about 6 to about 13, preferably about 8 to about 12, especially preferably about 8 to about 11.

According to the process of this invention, the compound of formula (I) obtained as above is then hydrothermally treated in an aqueous medium at a temperature of about 100° to about 200° C. to obtain the desired hydrothermally treated product useful as an iron deficiency syndrome treating agent.

The hydrothermal treatment is carried out in an aqueous medium such as water. The compound of formula (I) to be hydrothermally treated may be in a form not containing the mother liquor by dehydration, washing with water, drying or other treatments. Or it may contain the mother liquor. For example, it may be the reaction product simply separated from the reaction system and containing a small amount of the mother liquor. Generally, it is preferred to use it in a form not containing much mother liquor. For example, the compounds of formula (1) obtained in step (1) is washed with water, and the resulting paste-like product is put in an autoclave together with water for hydrothermal treatment. The hydrothermal treatment is preferably carried out under sufficient stirring conditions. If the concentration of the compound of formula (I) in the aqueous medium is too high, the stirring tends to become insufficient. Accordingly, the concentration of the compound of formula (I) is, for example, not more than about 200 g/liter, generally about 50 to about 200 g/liter, preferably about 50 to about 150 g/liter, during the hydrothermal treatment.

The hydrothermal treatment is carried out at a temperature of about 100° to about 200° C. If the hydrothermal treatment is too low below the lower limit of the above temperature range, no substantial increase in oxidation resistance can be obtained. If it is higher beyond the upper limit, the crystal structure of the compound of formula (I) begins to be destroyed, and an increase in oxidation resistance cannot be achieved.

The hydrothermal treatment time is, for example, about 0.5 to about 40 hours, preferably about 2 to about 20 hours. If the time is too short, it is difficult to obtain an improving effect. If the time is too long, a further increase in effect cannot be expected. The treatment time is therefore preferably selected within the above-exemplified range depending upon the treating temperature, the treating conditions, etc.

The treating pressure is atmospheric pressure to about 15 kg/cm$^2$. When the hydrothermal treatment is carried out in an autoclave according to a preferred embodiment, the pressure is, for example, from the autogeneous pressure (about 1 kg/cm$^2$) to about 15 kg/cm$^2$. As desired, the hydrothermal treatment may also be carried out in a non-oxidizing atmosphere such as nitrogen or another inert gas.

The hydrothermally treated product obtained as above may be dehydrated and dried preferably in a non-oxidizing atmosphere, for example under reduced pressure in an atmosphere of an inert gas such as nitrogen, helium and argon, or in a reducing atmosphere such as hydrogen.

The hydrothermally treated product of the compound of formula (I) obtained as above has improved oxidation resistance (stability) over the untreated compound of formula (I). For example, when left to stand in the air for several days, it does not substantially undergo oxidation and can retain its excellent function as an iron deficiency syndrome treating agent. When it is suspended in water after the hydrothermal treatment without drying, it does not undergo substantial oxidation for a long period of time and can retain its excellent function as an iron deficiency syndrome treating agent. Accordingly, it has much better handleability and storability than the non-treated compound of formula (I) and is useful as an excellent iron deficiency syndrome treating agent. It may be stored in a sealed condition, and it is not necessary to store it under reduced pressure, or in the presence or an inert gas or a reducing gas. For long-term storage, however, such a method of storing may be employed.

The hydrothermally treated product derived from the compound of formula (I) has extremely low toxicity as expressed by its LD$_{50}$ in mice (oral) of at least 7,000 mg/kg.

The hydrothermally treated product of this invention derived from the compound of formula (I) is useful for preventing, curing or otherwise treating an iron deficiency syndrome in man and other animals by administering it either as such or as a composition in any desired dosage form together with pharmaceutically acceptable diluents or carriers with or without other additives or adjuvants.

Thus, the present invention also provides a composition for increasing at least one of hemoglobin and the serum iron level, said composition being composed of (1) an amount, effective for increasing at least one of hemoglobin and the serum iron level, of the hydrothermally treated product of the invention and (2) a pharmaceutically acceptable diluent or carrier.

The invention also provides a method for increasing at least one of hemoglobin and the serum iron level, which comprises orally administering an amount, effective for increasing at least one of hemoglobin and the serum iron level, of the hydrothermally treated product of the invention.

Oral administration is a preferred route of administration. The dosage can be varied properly depending upon the type of the iron deficiency disease to be treated, its severity, the route of administration, the administration period, etc. In terms of the amount of the hydrothermally treated product of the invention as the active ingredient, the suitable dosage is, for example, about 50 to about 2,000 mg per day per adult (body weight 60 kg). Preferably, a dosage of about 50 to about 400 mg may be administered per day in one to three portions.

The iron deficiency treating agent of the invention may be in various forms, such as powders, granules, pills, tablets, capsules, suspensions and emulsions. It may also be in the form of pastes, chewing gums and drinks.

In preparing pharmaceutical compositions in these various forms, pharmaceutically acceptable diluents or carriers and other additives and adjuvants may be utilized. Known liquid or solid diluents or carriers and other additives and adjuvants generally used in the art may be properly selected and used. Examples include water, alcohols, various oils and fats of the vegetable or animal origin, various synthetic oils and fats, lactose, starches, dextrin, glucose, sucrose, refined sugar, yeast extracts, yolk, albumin, agar, gelatin, lanolin, millet jelly, glycerol, aluminum hydroxide gel, synthetic aluminum silicate, silicic anhydride, talc, kaolin, barium sulfate, magnesium sulfate, sodium chloride, potassium bromide, potassium iodide, boric acid, magnesium oxide, calcium phosphate, magnesium carbonate, calcium carbonate, sodium hydrogen carbonate, potassium hydrogen carbonate, citric acid, citrate salts, tartaric acid, tartrate salts, potassium hydrogen tartrate, calcium lactate, stearic acid, magnesium stearate, calcium stearate, alginic acid, alkali metal alginates, acetylsalicilic acid, ascorbic acid, ascorate salts, reduced glutathione, tragacanth gum, gum arabic, methyl cellulose, ethyl cellulose, carboxymethyl cellulose, carboxymethyl cellulose salts, polyvinylpyrrolidone, polyethylene glycol, sorbitan monostearate, fatty acid monoglycerides, and other surface-active agents and emulsifiers. Among them, reducing substances such as ascorbic acid or reduced glutathione are preferred because they further increase the absorption of the iron component of the hydrothermally treated product as the active ingredient according to the invention. It is also possible to incorporate other pharmaceutical substances such as sedatives, antacids and vitamins, preservatives, stabilizers, sweetenings and flavoring agents into the treating agent of the invention.

Preparation of the hydrothermally treated product of the invention into compositions in dosage forms can be performed by methods known per se.

The content of the hydrothermally treated product of the invention in the iron deficiency treating composition of this invention can be properly selected, and is, for example, about 30 to about 95% by weight, based on the total weight of the composition.

The hydrothermally treated product according to the invention can be advantageously used for the prevention and therapy of diseases associated with iron deficiency. Specifically, these diseases include, for example, iron deficiency anemia, hypoferremia, hypochromic anemia, hookworm anemia, juvenile anemia, chlorosis, nutritional anemia, achlorhydric anemia and physiological anemia.

The present invention is further illustrated by the following examples.

EXAMPLES 1 TO 3 AND COMPARATIVE EXAMPLES 1 AND 2

An aqueous solution of ferrous chloride ($Fe^{2+} = 1.0$ mole/liter), an aqueous solution of aluminum chloride ($Al^{3+} = 0.5$ mole/liter) and an aqueous solution of sodium hydroxide (2 moles/liter) were prepared. Each of the above solutions was prepared by dissolving each of the salts in water from which dissolved oxygen had been almost completely removed by boiling water for about 30 minutes and blowing high-purity nitrogen gas into it to saturation. Each of the aqueous solutions was maintained in an atmosphere of highly pure nitrogen gas. The three aqueous solutions were fed into a four-necked reactor equipped with a stirrer and purged with highly pure nitrogen gas through three ports in a completely sealed condition by means of metering pumps, and reacted at a temperature of 40±1° C. and a pH of about 8 to 9 while maintaining the $Fe^{2+}/Al^{3+}$ mole ratio at 2 to perform coprecipitation. The resulting slurry was dehydrated in an atmosphere of highly pure nitrogen and then washed with an aqueous solution of sodium carbonate in a concentration of 0.2 mole/liter (prepared by using the deoxygenated water stated above) to exchange Cl in the compound of formula (I) with $CO_3^{2-}$. Subsequently, the product was washed with water, and suspended in deoxygenated water to a solids concentration of about 100 g/liter. Two liters of the suspension was placed in each of three 3-liter autoclaves. The autoclaves were purged with highly pure nitrogen gas, and the hydrothermal treatment of the resulting compound of formula (I) was carried out for 15 hours at 150° C. in one autoclave, at 150° C. in another autoclave, and at 170° C. in still another autoclave.

The products were then taken out from the autoclaves, dehydrated and dried in vacuum. The dried products were chemically analyzed and found to have the following chemical composition.

$$(Fe^{2+})_4Al_2(OH)_{12}CO_3 \cdot 3H_2O$$

The dried products were white to light green, and the powder X-ray diffraction of these products showed a pattern similar to hydrotalcite.

When this compound was oxidized, it assumed a brown color. Two grams of each of the spherical dried products having a diameter of 2 mm obtained under the different hydrothermally treating conditions was taken into a weighing bottle, and exposed to the air. The time which elapsed until the sample changed to brown was measured. The results are shown in Table 1.

For comparison, the same oxidation resistance test as in Example 1 was carried out on a sample obtained by the method of Example 1 but not subjected to the hydrothermal treatment (Comparative Example 2) and a sample obtained by the method of Example 1 except that the hydrothermal treatment was carried out at 250° C. for 15 hours (Comparative Example 1). The results are also shown in Table 1.

As a result of the oxidation resistance test, the samples of this invention which were hydrothermally treated were oxidized only at their surfaces which changed to light brown. They, however, showed no change in color in their inside. They were very stable in this state, and even after the lapse of about 6 months, retained this state. In contrast, the sample of Comparative Example 2 changed in color completely even in its inside in 3 minutes, indicating its inability to be stored in the dried state in the air for a long period of time.

When stored as suspended in water or in a sealed condition, the samples of this invention were very stable to oxidation, and upon storage for about 6 months, no change in color was observed.

TABLE 1

|  | Hydrothermal treatment temperature (°C.) | Time which elapsed until the surface of the crystals changed to brown (hours) |
|---|---|---|
| Example 1 | | |
| 2 | 150 | 84 |
| 3 | 170 | 92 |
| Comp. Ex. 1 | 250 | The crystals decomposed, and lost their hydrotalcite-like crystal structure. |
| Comp. Ex. 2 | — | 3 minutes |

EXAMPLES 4 TO 8 AND COMPARATIVE EXAMPLE 3

Ferrous sulfate and aluminum sulfate were dissolved in water oxygenated as in Example 1 to prepare aqueous solutions having a total concentration of $Fe^{2+}$ and $Al^{3+}$ of 1 mole/liter and an $Fe^{2+}/Al^{3+}$ mole ratio of 5, 4, 3, 2, and 1, respectively. The aqueous solutions were kept in an atmosphere of highly pure nitrogen. Likewise, potassium hydroxide was dissolved in deoxygenated water to prepare a 2 mole/liter aqueous solution. In a reactor purged with highly pure nitrogen, the aqueous solution of ferrous sulfate and aluminum sulfate and the aqueous solution of potassium hydroxide were reacted with stirring at a pH of 9 to 9.5 and a temperature of 30±1° C. to perform coprecipitation. The resulting slurry was dehydrated in an atmosphere of highly pure nitrogen, and suspended in deoxygenated water to form a suspension having a solid concentration of about 50 g/liter. Two liters of each of the samples was put in a 2-liter autoclave and the inside atmosphere was purged with highly pure nitrogen. The sample was then hydrothermally treated at 150° C. for 10 hours. The product was taken out from the autoclave, and in an atmosphere of highly pure nitrogen, dehydrated, dried and molded into tablets having a diameter of 12 mm and a thickness of 5 mm. One tablet was put in a weighing bottle, and exposed to air at room temperature. The time which elapsed until the surface of the tablet changed to a brown color was measured. The results were shown in Table 2.

Separately, the dried products were each chemically analyzed, and subjected to powder X-ray diffraction. The compositions of the products obtained as a result of the chemical analysis are shown in Table 2. These samples commonly showed a powder X-ray diffraction pattern similar to that of hydrotalcite.

For comparison, a sample dried in an atmosphere of highly pure nitrogen without hydrothermal treatment was exposed to air. The change at this time is shown in Table 2.

TABLE 2

| | Chemical composition | Time which elapsed until the surface changed to a brown color (hours) |
|---|---|---|
| Example | | |
| 4 | $(Fe^{2+})_{10}Al_2(OH)_{24}SO_4 \cdot 7H_2O$ | 42 |
| 5 | $(Fe^{2+})_8Al_2(OH)_{20}SO_4 \cdot 6H_2O$ | 65 |
| 6 | $(Fe^{2+})_6Al_2(OH)SO_4 \cdot 4H_2O$ | 78 |
| 7 | $(Fe^{2+})_4Al_2(OH)_{12}SO_4 \cdot 2H_2O$ | 81 |
| 8 | $(Fe^{2+})_2Al_2(OH)_{4.4}(SO_4)_{0.8} \cdot 0.8H_2O$ | 48 |
| Comp. Ex. 3 | $(Fe^{2+})_4Al_2(OH)_{12}SO_4 \cdot 1.7H_2O$ | 40 minutes |

After the lapse of 6 months, the samples of Examples 4 and 8 changed to brown only on the tablet surfaces, and their insides showed white to light green. Thus, the oxidation occurred only on their surfaces, and the insides were stabilized. In contrast, the samples of Comparative Example 3 not subjected to hydrothermal treatment was completely oxidized to the inside in 2 minutes.

ADMINISTRATION EXAMPLE 1

Five healthy males having a body weight of 48 to 60 kg and aged 24 to 35 were used as subjects. The compound of this invention obtained in Example 1 and ferrous sulfate as a control were tested. On the day of testing, the subjects were caused to refrain from taking drugs other than the test drug, and foods such as egg and coffee and tea. The subjects were not allowed to take breakfast, but allowed to take lunch at 12:30, and dinner after drawing blood samples at 8:30. Immediately after the drawing of the blood samples, the drug was orally administered. The blood was taken from each of the subjects 2, 4, 6, 8, 10 and 12 hours after administration. From each of the blood samples 0.5 ml of serum was taken and colored with an Fe-direct reagent. The color obtained was spectrally analyzed at a wavelength of 535 nm to measure the serum iron level.

The control iron agent was dried ferrous sulfate ($FeSO_4$) in an amount of 400 g.

As an iron agent of this invention, 10 ml of the suspension obtained in Example 1 (containing 400 mg of the active component of the composition of this invention) was administered.

For comparison, the iron agent of Comparative Example 2 not subjected to hydrothermal treatment was tested in the same way.

The results are shown in FIG. 1. It is seen from FIG. 1 that the product obtained in Example 1 had a higher absorption than ferrous sulfate considered to have the best absorption, and its effect lasted for a long period of time. In FIG. 1, the solid line a shows the results obtained with the hydrothermally treated product of the invention; the solid line a', the examples of the iron agent of Comparative Example 2; and the broken line b, the results obtained with the ferrous sulfate.

ADMINISTRATION EXAMPLE 2

Five persons, aged between 30 and 36, including patients with iron deficiency anemia were used as subjects. The test drug was in the form of tablets prepared by mixing 90% of the compound of this invention obtained in Example 1, 9% of carboxy methyl cellulose as a disintegrant and 1% of magnesium stearate as a lubricant, and molding the mixture by a rotary tableting machine under a tableting pressure of 600 kg/cm² (one tablet weighing 136 mg contained 50 mg of $Fe^{2+}$). For about 1 month, each of the subjects was allowed to take orally one tablet of the test drug after breakfast and lunch every day. The blood was drawn before the administration, and 1 week, 2 weeks and 3 weeks after the administration. Each of the blood samples was examined for serum iron, hemoglobin and unsaturated iron binding capacity. The presence or absence of side-effects was also observed.

One hundred mg of dry ferrous sulfate ($FeSO_4$) was used as a control, and administered to other five persons including patients with iron deficiency anemia after breakfast and lunch. The same items as above were examined.

The unsaturated iron binding capacity was measured by the RIA method, and the hemoglobin value was measured by using the cyanomethohemoglobin method. The results are shown in Tables 3 and 4.

It is seen from the results that the treating agent of this invention exhibits a high iron absorption in adults with anemia as demonstrated by an increase in the amount of hemoglobin and the serum iron level, and no particular side effects were noted except that light constipation occurred in two subjects. Usually, to completely cure patients with anemia, an iron-containing drug should be administered successively over 1 to 2 months. The treating agent of this invention can fully meet this requirement, and shows good iron absorption with very much reduced side-effects.

On the other hand, iron sulfate heretofore used in treating anemia gave such side-effects as nausea, stomachache, abdominal pain, etc. 2 to 7 days after the start of the administration course, and the administration had to be stopped.

TABLE 3

Iron absorption and side-effects at the time of administering the compound of the invention

| Volunteer | Time of examination (after the start of the administration course)* | Hemo-globin (g/dl) | Serum iron (μg/l) | Unsaturated iron-binding capacity (μg/dl) | Side-effects |
|---|---|---|---|---|---|
| A (female) 36 years old | previous day | 12.1 | 45 | 431 | Tended to have constipation on the 6th day and thereafter; but no other subjective symptoms |
| | 7th day | 13.0 | 150 | 305 | |
| | 14th day | 13.4 | 186 | 234 | |
| | 21th day | 12.9 | 98 | 327 | |
| B (female) 34 years old | previous day | 5.3 | 20 | 551 | None |
| | 7th day | 6.2 | 58 | 506 | |
| | 14th day | 9.9 | 48 | 562 | |
| | 21th day | 11.5 | 85 | 470 | |
| C (female) 34 years old | previous day | 10.2 | 38 | 472 | Tended to have constipation on the 7th day and thereafter; but no other subjective symptoms |
| | 7th day | 11.5 | 230 | 223 | |
| | 14th day | 12.5 | 98 | 365 | |
| | 21th day | 13.6 | 96 | 334 | |
| D (female) 35 years old | previous day | 6.9 | 25 | 537 | None |
| | 7th day | 8.1 | 41 | 533 | |
| | 14th day | 9.4 | 68 | 542 | |

TABLE 3-continued

Iron absorption and side-effects at the time of administering the compound of the invention

| Volunteer | Time of examination (after the start of the administration course)* | Hemoglobin (g/dl) | Serum iron (μg/l) | Unsaturated iron-binding capacity (μg/dl) | Side-effects |
|---|---|---|---|---|---|
| | 21th day | 10.8 | 96 | 459 | |
| E (male) 30 years old | previous day | 15.0 | 115 | 265 | None |
| | 7th day | 15.9 | 80 | 295 | |
| | 14th day | 16.3 | 120 | 272 | |
| | 21th day | 16.1 | 118 | 232 | |

*The "previous day" means the day before the start of the administration course.

TABLE 4

Iron absorption and side-effects at the time of administering FeSO$_4$ (a conventional iron-containing drug)

| Volunteer | Time of examination (after the start of the administration course)* | Hemoglobin (g/dl) | Serum iron (g/l) | Unsaturated iron-binding capacity (g/dl) | Side-effects |
|---|---|---|---|---|---|
| F (female) 28 years old | Previous day | 7.5 | 24 | 561 | Because of strong nausea the administration was stopped on the third day. |
| | 3rd day | 8.1 | 62 | 533 | |
| G (female) 34 years old | Previous day | 12.1 | 43 | 442 | Stomachache occurred on the 4th day and thereafter, and the administration was stopped on the 6th day. |
| | 7th day | 13.0 | 144 | 308 | |
| H (female) 19 years old | Previous day | 9.7 | 28 | 493 | Abdominal pain began soon after the administration, and the administration was stopped on the 5th day. |
| | 5th day | 10.6 | 33 | 477 | |
| I (female) 21 years old | Previous day | 13.1 | 102 | 273 | Because of strong nausea, the administration was stopped on the 4th day. |
| | 4th day | 13.3 | 96 | 289 | |
| J (male) 32 years old | Previous day | 16.3 | 107 | 248 | Stomachache occurred on the 7th day and thereafter. The administration was stopped on the 7th day. |
| | 7th day | 15.5 | 115 | 265 | |

*The "previous day" means the day before the start of the administration course.

DRUG FORMULATION EXAMPLE 1

The following ingredients were mixed to form a powder.

| | |
|---|---|
| Powder of the compound obtained in Production Example I. | 500 parts by weight |
| Methyl cellulose | 20 parts by weight |
| Carboxy methyl cellulose | 10 parts by weight |
| Starch | 380 parts by weight |

DRUG FORMULATION EXAMPLE 2

The following ingredients were mixed and continuously tableted under a pressure of about 600 kg/cm$^2$ into tablets each weighing 200 mg.

| | |
|---|---|
| Powder of the compound obtained in Production Example I. | 675 parts by weight |
| Carboxy methyl cellulose | 145 parts by weight |
| Starch | 120 parts by weight |
| Vitamin C | 40 parts by weight |
| Magnesium stearate | 20 parts by weight |

DRUG FORMULATION EXAMPLE 3

The following ingredients were uniformly mixed by a homomixer to form a suspension.

| | |
|---|---|
| Powder of the compound obtained in Production Example 2. | 200 parts by weight |
| Methyl paraben | 1 parts by weight |
| Propyl paraben | 0.5 parts by weight |
| 70% Sorbitol solution | 11 parts by weight |
| Peppermint | 0.14 parts by weight |
| Water | 800 parts by weight |

What we claim is:

1. A hydrothermally treated product of a compound having a hydrotalcite-like crystal structure and represented by the following formula (I)

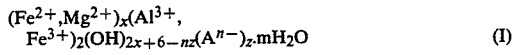
$$(Fe^{2+}, Mg^{2+})_x (Al^{3+}, Fe^{3+})_2 (OH)_{2x+6-nz} (A^{n-})_z \cdot mH_2O \qquad (I)$$

wherein A$^{n-}$ represents an anion having a valence of n, Mg$^{2+}$ is within the range of $0 \leq Mg^{2+} < x$, Fe$^{3+}$ is within the range of $0 \leq Fe^{3+} < 2$, x is a number represented by $1 \leq x < 20$, z is a number represented by $0 < z < 3$, and m is a number represented by $0 \leq m < 20$, the product being formed by the thermal treatment of the compound of formula (I) at a temperature of about 100° C. to about 200° C. in an aqueous medium.

2. The hydrothermally treated product of claim 1 wherein the compound (I) is represented by the following formula (I)'

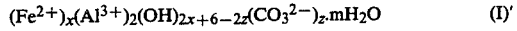
$$(Fe^{2+})_x (Al^{3+})_2 (OH)_{2x+6-2z} (CO_3^{2-})_z \cdot mH_2O \qquad (I)'$$

wherein x, z and m are as defined in claim 1.

3. The hydrothermally treated product of claim 1 or 2 wherein x is a number represented by $2.5 \leq x < 8$.

4. The hydrothermally treated product of claim 1 wherein A$^{n-}$ is an anion selected from the group consisting of $CO_3^{2-}$, $SO_4^{2-}$, $OH^{-1}$, $(CHOHCOO)_2^{2-}$, $(CHOH)_4CH_2OHCOO^{1-}$, $C_2H_2(COO)_2^{2-}$, $(CH_2COO)_2^{2-}$, $C_5H_9O_5COO^{1-}$, $CH_2NH_2COO^{1-}$ and $CH_3CHOHCOO^{1-}$.

5. A composition for increasing at least one of hemoglobin and the serum iron level, said composition comprising (1) an amount, effective for increasing at least one of hemoglobin and the serum iron level, of a hydrothermally treated product of a compound having a hydrotalcite-like crystal structure and represented by the following formula (I)

$$(Fe^{2+}, Mg^{2+})_x (Al^{3+}, Fe^{3+})_2 (OH)_{2x+6-n-z} (A^{n-})_z \cdot mH_2O \qquad (I)$$

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, z is a number represented by $0 < z < 3$, and m is a number represented by $0 \leq m < 20$, the product being formed by the thermal treatment of the compound of formula (I) at a temperature of about 100° C. to about 200° C. in an aqueous medium, and (2) a pharmaceutically acceptable diluent or carrier.

6. The composition of claim 5 wherein said compound (I) is represented by the following formula (I)'

$$(Fe^{2+})_x (Al^{3+})_2 (OH)_{2x+6-2z} (CO_3^{2-})_z \cdot mH_2O \qquad (I)'$$

wherein x, z and m are as defined in claim 5.

7. The composition of claim 5 or 6 wherein x is a number represented by $2.5 \leq x < 8$.

8. The composition of claim 5 wherein the amount of the compound (I) is about 30 to about 95% based on the total weight of the composition.

9. A method for increasing at least one of hemoglobin and the serum iron level, which comprises orally administering an amount, effective for increasing at least one of hemoglobin and the serum iron level, of a hydrothermally treated product of a compound having a hydrotalcite-like crystal structure and represented by the following formula (I)

$$(Fe^{2+}, Mg^{2+})_x (Al^{3+}, Fe^{3+})_2 (OH)_{2x+6-n-z} (A^{n-})_z \cdot mH_2O \qquad (I)$$

wherein $A^{n-}$ represents an anion having a valence of n, $Mg^{2+}$ is within the range of $0 \leq Mg^{2+} < x$, $Fe^{3+}$ is within the range of $0 \leq Fe^{3+} < 2$, x is a number represented by $1 \leq x < 20$, z is a number represented by $0 < z < 3$, and m is a number represented by $0 \leq m < 20$, the product being formed by the thermal treatment of the compound of formula (I) at a temperature of about 100° C. to about 200° C. in an aqueous medium.

10. The method of claim 9 wherein the compound (I) is represented by the following formula (I)'

$$(Fe^{2+})_x (Al^{3+})_2 (OH)_{2x+6-2z} (CO_3^{2-})_z \cdot mH_2O \qquad (I)'$$

wherein x, z and m are as defined in claim 9.

11. The method of claim 9 or 10 wherein the dosage of the hydrothermally treated product is about 50 mg to about 2,000 mg per day per adult.

12. The method of claim 9 or 10 for treating a patient suffering from anemic symptoms.

* * * * *